United States Patent

Henco et al.

[11] Patent Number: 5,849,545
[45] Date of Patent: Dec. 15, 1998

[54] SUBSTRATE MATERIAL FOR SIMULTANEOUSLY BINDING GENOTYPIC AND PHENOTYPIC SUBSTANCES

[75] Inventors: Karsten Henco, Erkrath; Manfred Eigen, Gottingen, both of Germany

[73] Assignee: Evotec Biosystems GmbH, Hamburg, Germany

[21] Appl. No.: 834,834

[22] Filed: Apr. 10, 1997

Related U.S. Application Data

[63] Continuation of Ser. No. 432,121, filed as PCT/EP93/03075 Nov. 3, 1993, published as WO94/10572, abandoned.

[30] Foreign Application Priority Data

May 11, 1992 [DE] Germany .......................... 42 373 81.6

[51] Int. Cl.⁶ .................................................. C12P 19/34
[52] U.S. Cl. ............................ 435/91.2; 435/91.5; 435/5; 536/24.3
[58] Field of Search ................................ 435/91.2, 91.5, 435/5, 174, 175; 536/24.3

[56] References Cited

U.S. PATENT DOCUMENTS

| | | | |
|---|---|---|---|
| 4,379,843 | 4/1983 | Cashion | 435/179 |
| 4,873,192 | 10/1989 | Kunkel | 435/91.5 |
| 5,143,854 | 9/1992 | Pirrung et al. | 436/518 |

FOREIGN PATENT DOCUMENTS

WO9218645  10/1992  WIPO .

OTHER PUBLICATIONS

Berichte Der Bunsen–Gesellschaft Fur Physikalische Chemie vol. 89, No. 6, Jun. 1985, pp. 658–667; "Macromolecular Evolution: Dynamical Ordering in Sequence Space".

Abstract of Hunger et al patent DD–274676, (1990).

*Primary Examiner*—Scott W. Houtteman
*Attorney, Agent, or Firm*—Jacobson, Price, Holman & Stern, PLLC

[57] ABSTRACT

Described is a support material that can simultaneously bind both genotypic and phenotypic substances. The respective areas, which can have surface-modifying matter such as anionic exchangers and/or affinity ligands, simultaneously bind, for example, nucleic acids and proteins or peptides. The support materials described can be used in processes for evolutive optimization of biopolymers, wherein genotype and phenotype can be bound at the same time so as to furnish them for further analysis.

15 Claims, No Drawings

SUBSTRATE MATERIAL FOR SIMULTANEOUSLY BINDING GENOTYPIC AND PHENOTYPIC SUBSTANCES

This application is a continuation of application Ser. No. 8/432,121, filed as PCT/EP93/03075 Nov. 3, 1993 published as WO94/10572, now abandoned.

The present invention pertains to a substrate material and a process for evolutive optimization of biopolymers.

Evolutive biotechnology is a novel technique which quasi mimics Evolution in the test tube to obtain mutated and optimized nucleic acid structures solely through replication mechanisms. Replication of the nucleic acid is performed with appropriate enzyme systems, such as polymerases, the natural misreading rate of which is made use of to create a distribution of quasi-species derived from a particular nucleic acid molecule or ensemble. More details about this technique are described in the German Patent Specification No. 41 12 440 C 2.

However, a common feature of the techniques of evolutive biotechnology is the necessity of parallel processing of a large number of samples to provide evolutive optimization within a technically practical period of time. Thus, for instance, systematic optimization of a particular phenotype, such as an enzyme, by methods of mutagenesis of the encoding gene is sought. Such a process which functions according to the method of so-called irrational or evolutive design thus requires screening on the basis of certain desired functions of the phenotypes obtained. When a desired phenotype has been found, immediate access to the encoding gene, i.e. the corresponding nucleic acid, is essential. Although indirect methods of obtaining the encoding sequence, e.g. by protein sequencing and transforming the sequence into the corresponding gene sequence, are technically possible, they are hardly practical due to their technical complexity.

In addition, performing evolutive biotechnology in a technically reasonable way requires parallel performance, for a multitude of individual transformed cells, of locally fixed specific purification of phenotypes and genotypes in a separation process, i.e. parallel performance of about $10^6$–$10^8$ experiments.

Thus, the invention is based on the technical problem of providing a system which allows for the common purification of a genotype and a phenotype, e.g. of a protein and its corresponding encoding gene, and hence providing a process which allows for evolutive optimization of biopolymers. This substrate system in combination with a growth medium is intended simultaneously to allow for localized growth of a cell colony or for a corresponding enzymatic gene amplification system to be employed in which the genotype remains locally coupled to its phenotype and is maintained within a localized element without intermingling with other genotypes or phenotypes.

This problem is solved by a substrate material having at least two simultaneous binding properties for the respective specific binding of genotypic substances and phenotypic substances. This avoids ready mixing of different genes or genotypes and on the other hand has the effect that enzyme systems which have derived, as phenotypes, from said genotypes (information carriers) remain associated with their respective genes and hence can be isolated in principle. This substrate system is characterized in that the substrate material according to the invention can bind the genotypical substances to respective particular surface areas thereof whereas the phenotypical substances are bound by other surface areas of the substrate material. In a preferred embodiment of the substrate material according to the invention, nucleic acids, for instance, can be bound as the genotypical substances, and proteins or peptides, for instance, can be simultaneously bound as the phenotypical substances.

The substrate material according to the invention consists of areas which are capable of binding the genotype and/or the phenotype and are distanced from one another by <1,000 µm, preferably <100 µm, wherein the distance should not be less than 10 nm. Due to the different chemical natures of the genotype and phenotype, those areas preferably have two different binding properties at the same time which are respectively specific for the two substance classes mentioned, genotype and phenotype.

In particular, those areas can have ion-exchanging or affinity properties, such as hydrophobic interaction properties, or complex forming properties, or combinations thereof. Thus, it is possible, for instance, that when areas having affinity properties are used the genotype is recognized in the corresponding areas by particular affinity ligands, whereas the phenotype can interact with some other affinity ligand which is also present in the corresponding areas. Thus, the molecules or molecular classes respectively representing phenotype or genotype can be bound to the substrate surface directly or through particular natural or artificially introduced substituents. Those substituents may be haptens or biotin or avidin or other appropriate sidechains, such as certain oligopeptides. It can also be advantageous, however, to use a substrate material which has affinity properties in one portion of the areas and ion-exchanging properties in other portions of the same areas.

With a surface modified by affinity ligands, the substrate material according to the invention should allow for reversible interactions with the bound genotypes or phenotypes thereby enabling elution of at least one of the molecular types (genotype or phenotype) bound.

The substrate material comprising the areas having binding properties for genotype and phenotype is preferably located on or within a matrix, such as a membrane or assembly of membranes, sheet, wafer, capillary, fibers or fibrous composite structure, such as woven or non-woven fabrics, or combinations of such objects.

It can also be advantageous to provide a substrate material with areas having an affinity to at least one protein or peptide, but which can bind nucleic acids at the same time. Such material can practically be considered a hybride of ion-exchanging and affinity chromatographic materials. Thus, this group-specific binding property for nucleic acids and proteins allows for simultaneous binding of nucleic acids and proteins. Standardization is possible by the fact that within a particular volume element specific protein bonds can occur only in defined numbers.

As ion-exchanging materials for the areas of the substrate material according to the invention, large-pore or non-pore materials are preferably used which are still capable of binding polyanions, such as DNA, at an ionic strength comparable to that of sodium chloride at a concentration of 1M. In particular, large-pore silica gels, such as those described in DE 32 11 309 which are commercially available under the designation of QIAGEN, have proven useful. Affinity ligands may be, for instance, biotin derivatives and/or streptavidin derivatives and/or avidin derivatives and/or nucleic acids and/or antibody fragments and/or metal chelates and/or peptide ligands. If anion-exchanging materials and affinity materials on different particular substrates are coupled, both these particle types can be intimately mixed such that both binding properties can be found in the areas of the substrate according to the invention. If the areas are located on fibrous substrates, the same effect can be attained by interweaving or co-pressing the fibers or else by close contact of thin membranes of which at least one membrane must be passable for at least one of the substance classes. A reticular substrate may also be used which comprises, at both of its sides, the respective binding properties for one of the molecular types, genotype or phenotype.

The use of the substrate materials according to the invention serves the spatially close binding of two different molecules, such as proteins and/or nucleic acids which can code for the corresponding proteins, for instance. The substrate according to the invention can be used to particular advantage in evolutive optimization of biopolymers, especially for parallel analysis of different gene products and their related genes.

Thus, a process for evolutive optimization of biopolymers is provided in which the genotype and phenotype can be simultaneously bound to one substrate material and selectively or concurrently isolated.

The process according to the invention preferably proceeds in a reaction chamber in which the structural type representing the genotype, for instance, a nucleic acid, is subjected to mutagenesis, this structural type is subjected to at least one replication step, expressed in an expression system, and the corresponding expression product (phenotype), for instance, a protein, is bound to the substrate material along with the genotype, for instance, a nucleic acid coding for this protein, and examined for specific properties having been optimized.

Proteins and/or nucleic acids can used for test purposes and for further processing. The combination of, on one hand, metal chelate chromatography based on nickel-NTA-coupled solid phase carriers capable of extracting proteins containing a succession of 6 histidines from aqueous solution and binding them in a complex and, on the other hand, anion-exchange chromatography for the extraction and purification of nucleic acids has proven particularly advantageous. In particular, this combination can be arranged on a membrane or a one-dimensional fabric whereby, in the presence of an appropriate culture medium, cell colonies can be localized and separately cultured.

However, instead of cells, cell-free systems, such as enzymatic amplification systems, can also be employed as replication systems for genes. In this case, the areas of the substrate according to the invention practically serve as compartments in each of which reactions can take place between reactants without interacting with the other areas. This is ensured by the surfaces involved which prevent diffusion processes of the macromolecules. Thus, enzymatic amplifications can be performed without mixing of the amplification products from different master sequences. This enables the establishment of a distribution of quasi-species within the space limits of the respective areas.

The following membrane has proven to be a particularly useful embodiment. On this membrane, particular areas are present which preferably consist of anion-exchanging materials according to DE-A-32 11 309 C 2 and materials modified with nitrilotriacetic acid and/or the corresponding nickel chelates of this substance class. The membrane was processed according to the so-called enmejh process (of the 3M company, St. Paul, U.S.A.). The substrate material according to the invention can be employed in a process which, in particular, allows for the following:

comparative screening of approximately $10^6$–$10^8$ clones in one experiment;

phenotype/genotype coupling, i.e. direct access to the corresponding gene of a protein once having been characterized as optimal;

quantified comparison of the enzymatic activities of cell-contained or secreted proteins;

using prokaryotic or eukaryotic cells;

automatic operation and testing for particular properties;

standardization of recombinant proteins;

recovery of the specifically bound proteins and nucleic acids; and strategically conducted evolutionary improvement of protein structures.

The advantages of employing the substrate material according to the invention are illustrated in more detail by the following example:

A membrane saturated with culture medium serves to accommodate recombinant cells. Following the transformation of competent *Escherichia coli* cells and determination of the concentration of competent cells in the medium, the cell suspension is applied to the membrane by means of a piezo automatic pipetting device such that on average one cell is deposited per droplet and element of area. This element of area is selected depending on the amount of cells to be positioned within a raster of 0.1–1 mm distances. Thus, $10^6$–$10^8$ cells per $m^2$ can be positioned. Additional candidate competent cells are Bacillus subtilis or Baculovirus infected insect cells.

The transformed competent cells are cultured for a period corresponding to about 20 replication cycles so that about $10^6$ cells are derived from one recombinant cell. This is followed by induction of the recombinant protein by either chemical or thermal induction with continued culturing for a period of about 1–12 hours. The transformed nucleic acids code for an amino acid sequence in the corresponding protein containing 6 histidine residues. Once these proteins are being secreted, the proteins thus labeled are bound by the areas having nitrilotetraacetic acid modified surfaces. The corresponding nucleic acid, following release thereof by lysis of the cells, is also bound, however, it is bound on the ion-exchange material which is present in the area of the substrate according to the invention.

The membrane is washed to remove cell fragments and other components and assayed.

The ion-exchanging material QIAGEN has the particular advantage of being capable of binding nucleic acids without degradation of the bound nucleic acid even under unfavorable environmental conditions. The bound nucleic acid, e.g. DNA, is released only by elution with high concentrations of salt.

After the membrane has been assayed, the nucleic acids of the mutants having the highest activity are eluted from the corresponding areas and can be used for another cycle in an evolutive biotechnology process.

The process according to the invention allows for a good evaluation of the fitness landscape surrounding a particular mutant by combining it with automatic sequencing methods.

We claim:

1. A substrate material having at least two simultaneous binding properties for the respective specific binding of nucleic acids and their corresponding expression products, wherein a) said substrate material has a first surface area capable of binding only said nucleic acids and, separate from said first surface area, a second surface area capable of binding only said expression products, and one of said first and second surface areas has affinity properties effected by a first affinity ligand or ligands and the other said surface area has ion-exchange or affinity properties effected by a second affinity ligand or ligands, said affinity properties of said first surface area differing from said affinity properties of said second surface area or b) said substrate material is capable of binding said nucleic acids and said expression products over the entire surface area, said surface area having a first portion with affinity properties effected by a first affinity ligand or ligands and a second portion with ion-exchange or affinity properties effected by a second affinity ligand or ligands, said affinity properties of said first portion differing from said affinity properties of said second portion.

2. The substrate material according to claim 1, wherein said first surface area and said second surface area are separated from one and another by 10 nm to 1,000 μm.

3. The substrate material according to claim 1, wherein complex forming properties are said affinity properties.

4. The substrate material according to claim 1, wherein hydrophobic interactions are said affinity properties.

5. The substrate material according to claim 1, wherein at least one of said first and second surface areas having affinity properties allows for reversible interactions enabling elution of at least one of the molecular types bound.

6. The substrate material according to claim 1, wherein said substrate material is located two-dimensionally on a membrane or assembly of membranes or embedded within a membrane.

7. The substrate material according to claim 1, wherein said substrate material is located in a capillary or on a fiber or fibrous composite structure or combinations thereof.

8. The substrate material according to claim 7, wherein a non-woven fabric is said fibrous composite structure.

9. The substrate material according to claim 1, wherein the other surface area has anion-exchange properties.

10. The substrate material according to claim 9, wherein the other surface area having said anion-exchange properties are provided by surface-modified large-pore or close-pore particles.

11. The substrate material according to claim 9, wherein the other surface area having said anion-exchange properties is still capable of binding DNA molecules at an ionic strength corresponding to that of 1M NaCl.

12. The substrate material according to claim 1, wherein at least one of said first and second surface areas having said affinity properties is constituted by biotin derivatives, streptavidin derivatives, avidin derivatives, nucleic acids, antibody fragments, metal chelates, protein ligands, peptide ligands, or a combination of protein and peptide ligands.

13. The substrate material according to claim 9, wherein said areas having said affinity properties are constituted by metal chelates based on nickel-nitrilotriacetic acid chelates and said areas having said anion-exchange properties are constituted by materials capable of binding nucleic acids.

14. A process for evolutive optimization of biopolymers comprising applying nucleic acids and their corresponding expression products simultaneously to the substrate, material according to claim 1, and isolating said nucleic acids and their corresponding expression products selectively or concurrently.

15. A process comprising the sequential steps of:

subjecting a nucleic acid to mutagenesis in a reaction chamber to effect a mutagenized nucleic acid;

subjecting the mutagenized nucleic acid to at least one replication;

expressing the mutagenized nucleic acid to effect an expression product;

binding the expression product along with the nucleic acid on a substrate material having at least two simultaneous binding properties for the respective specific binding of nucleic acids and their corresponding expression products, wherein a) said substrate material has a first surface area capable of binding only said nucleic acids and, separate from said first surface area, a second surface area capable of binding only said expression products, and one of said first and second surface areas has affinity properties effected by a first affinity ligand or ligands and the other said surface area has ion-exchange or affinity properties effected by a second affinity ligand or ligands, said affinity properties of said first surface area differing from said affinity properties of said second surface area or b) said substrate material is capable of binding said nucleic acids and said expression products over the entire surface area, said surface area having a first portion with affinity properties effected by a first affinity ligand or ligands and a second portion with ion-exchange or affinity properties effected by a second affinity ligand or ligands, said affinity properties of said first portion differing from said affinity properties of said second portion; and examining the bound expression product.

* * * * *